United States Patent
Santilli et al.

[11] 3,974,162
[45]*Aug. 10, 1976

[54] 4-PYRIMIDINYLTHIOACETIC ACID DERIVATIVES

[75] Inventors: Arthur A. Santilli, Havertown; Anthony C. Scotese, King of Prussia; Rudolph R. Tomarelli, Phoenixville, all of Pa.

[73] Assignee: American Home Products Corporation, New York, N.Y.

[ * ] Notice: The portion of the term of this patent subsequent to June 4, 1991, has been disclaimed.

[22] Filed: Dec. 21, 1972

[21] Appl. No.: 317,343

[52] U.S. Cl.................. 260/256.5 R; 260/249.5; 260/251 R; 260/256.4 C; 260/256.4 N; 424/249; 424/251
[51] Int. Cl.².................................. C07D 239/38
[58] Field of Search............................ 260/256.5 R

[56] References Cited
UNITED STATES PATENTS

| | | |
|---|---|---|
| 2,347,992 | 5/1944 | D'Alelio et al................ 260/256.5 R |
| 2,352,945 | 7/1944 | D'Alelio et al................ 260/256.5 R |
| 2,621,182 | 12/1952 | Hitchings et al.............. 260/256.5 R |
| 3,814,761 | 6/1974 | Santilli et al................. 260/256.5 R |

*Primary Examiner*—R. Gallagher
*Attorney, Agent, or Firm*—Richard K. Jackson

[57] ABSTRACT

The compounds

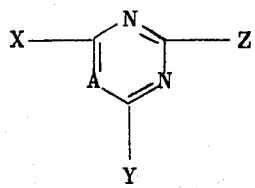

in which the symbol A represents a carbon or nitrogen atom, X represents —Cl, lower alkoxy or the substituted amino group

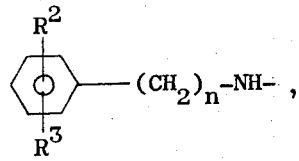

Y represents —Cl, lower alkoxy,

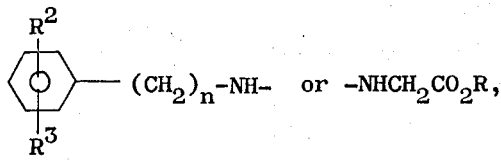

with the proviso that when Y is —Cl, X and Z are other than —Cl, and Z represents —H, —Cl, —OCH$_2$CO$_2$R, —SCH$_2$C≡CH,

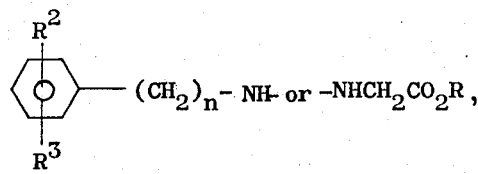

wherein R and R² are —H or lower alkyl, R³ is —H, —Cl or lower alkyl, and n represents one of the integers 0 and 1, exhibit anti-lipemic activity and/or central nervous system depressant activity in warm-blooded animals.

4 Claims, No Drawings

4-PYRIMIDINYLTHIOACETIC ACID DERIVATIVES

BACKGROUND OF THE INVENTION

Anti-lipemic agents in current use include such diverse compounds as ethyl p-chlorophenoxyisobutyrate (clofibrate), nicotinic acid, thyroxine, certain estrogens and the bis(p-chlorophenyl)-acetal of 1-methyl-4-piperidyl glyoxylate.

DESCRIPTION OF THE INVENTION

In accordance with this invention, there is provided certain novel anti-lipemic agents presenting the structures

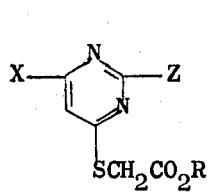 and 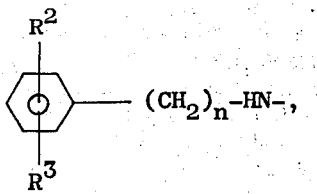

X is —Cl or 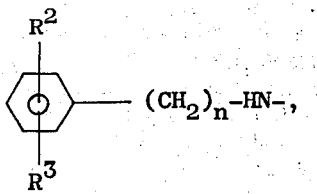,

Z is —H or 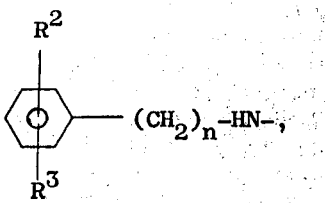,

R is —H or lower alkyl,
$R^2$ is —H or lower alkyl,
$R^3$ is —H; lower alkyl or —Cl, and
n represents one of the integers 0 and 1.

In addition to the anti-lipemic activity of the compounds described supra, central nervous system depressant activity was found to reside in the compounds as a group represented by the formula:

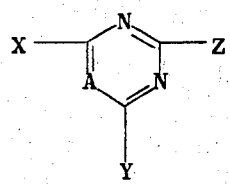

in which the symbol A represents a carbon or nitrogen atom, X represents —Cl, lower alkoxy or the substituted amino group

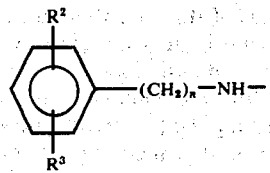

Y represents —Cl, lower alkoxy,

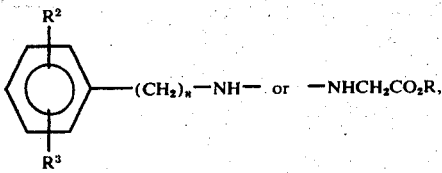

with the proviso that when Y is —Cl, X and Z are other than —Cl, and Z represents -H, —Cl, -OCH$_2$CO$_2$R, -SCH$_2$C ≡ CH,

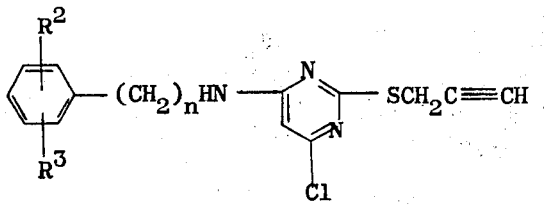

wherein R and $R^2$ are —H or lower alkyl, $R^3$ is —H, —Cl or lower alkyl, and n represents one of the integers 0 and 1.

By the expression lower alkyl applicants intend to embrace monovalent, branched and unbranched aliphatic groups of paraffinic derivation containing from 1 to 7 carbon atoms.

The compounds of this invention are prepared from barbituric or cyanuric acid chloride by reaction with appropriately substituted alcohols, mercaptans and amines. Thus, for example, the anti-lipemic compounds, representing the preferred aspect of the invention, may be prepared in accordance with the following equation:

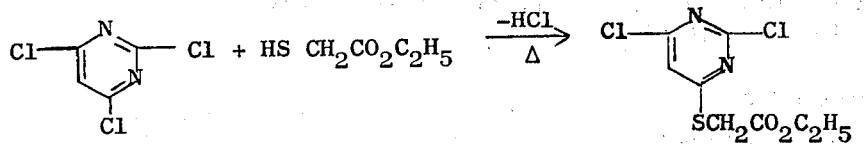

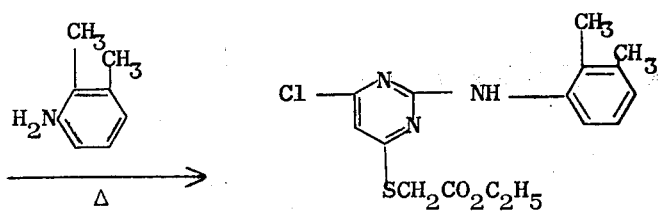

By analogous means the disclosed ether, thioether and amine derivatives are prepared. From the intermediate monochloro substituted pyrimidinylthio acetic acid esters, modification of the carboxylic acid funtional group is readily achieved by conventional techniques of transesterification, saponification and hydrolysis.

The anti-lipemic compounds of this invention reduce the concentration of cholesterol in blood serum in hypercholesterolemic rats.

The anti-lipemic activity of the compounds first described above, was established by orally administering the compounds being tested to each member of a group of young male rats which had been fed a hypercholesterolemic diet for three weeks and grouped, based upon their equal average serum cholesterol concentration determined on 0.01 milliliters of serum separated from tail blood collected in a capillary tube. The compounds tested were administered orally once or twice a day for three consecutive days. The serum cholesterol was determined on the fourth day and compared to the average of the group of untreated rats. The potency of the test compound is expressed as the percent activity of concomitantly run tests employing Atromid S (clofibrate) as the standard. The test procedure was repeated with normal chow-fed rats to determine the hypolipemic effect in the normal host.

The hypolipemic agents of this invention are effectively administrable orally or parenterally. The amount of the active compound needed to reduce the fat content of the blood to the desired level varies with the mode of administration to a certain extent as well as the condition of the individual under treatment with regard to age, fat concentration in the blood and depots, diet, transference factors of the gut and interstitial tissues and contributing factors such as the presence of hyperthyroidism, diabetes, cirrhosis of the liver or spleen, pancreatitis, etc.

In practice, the compounds are administered to one suffering from hyperlipemia in unit doses containing from 0.05 to 25 milligrams of active ingredient, the remainder of the formulation constituting known adjuvants. In human treatment, from 1 to 10 milligram and conventionally 5 milligram doses of the active compounds of this invention are considered to be most desirable from the standpoint of uniform presentation for controlled administration. The compounds of the invention may be administered alone or in combination with pharmacologically acceptable carriers, the proportion of which is determined by the chosen route of administration and standard pharmaceutical practice. For example, they may be administered orally in tablet or capsule form with conventional flavors, diluents, lubricants, disintegrators or binding agents as may be required. They may be administered orally in the form of a solution or they may be injected parenterally. For parenteral administration they may be used in the form of a sterile solution containing other solutes, for example, enough saline or glucose to make the solution isotonic.

Of the anti-lipemic compounds disclosed, the most active are those of Examples 1–4, infra, which exhibited minimal activity of 150 percent that of Atromid S at 10 milligrams per kilogram host body weight with the exception of [6-(p-chlorobenzylamino)-4-pyrimidinyl-thio]acetic acid ethyl ester, which was 55 percent as effective as the standard clofibrate.

As central nervous system depressants, the compounds are administered orally or intraperitoneally with or without a physiologically acceptable carrier. The depressant activity of the claimed compounds was established by oral and intraperitoneal administration of each compound tested to three mice weighing from 14 to 24 grams at each of the dosage levels 400, 127, 4.0 and 1.27 milligrams per kilogram body weight. The mice were then observed for at least two hours during which time signs of general stimulation (i.e. increased spontaneous motor activity, hyperactivity on tactile stimulation, twitching), general depression (i.e. decreased spontaneous motor activity, decreased respiration and autonomic activity (i.e. miosis, mydriasis, diarrhea) were noted. From the observations noted the depressant activity of the claimed compounds was found to lie within the dosage range 12.7 to 400 milligrams per kilogram host body weight, the latter dosage being the highest dose tested. The results of these observations for the tested compounds are presented infra in conjunction with the preparatory procedure used and are expressed in terms of the lowest dosage at which the given effect was observed.

EXAMPLE 1

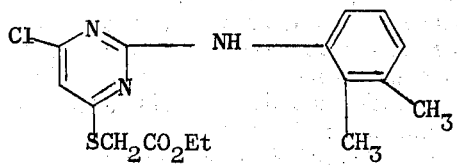

[6-Chloro-2-(2,3-xylidino)-4-pyrimidinylthio]acetic acid ethyl ester.

A mixture of 18.3 g. of 2,3,6-trichloropyrimidine, 10.6 g. of sodium carbonate and 12.0 g. of ethyl mercaptoacetate in 250 ml. of ethanol was heated with stirring under reflux for 3 hours. 2,3-Dimethylaniline (12.2 g.) was added and refluxing with stirring was continued overnight. The reaction mixture was filtered and the filtrate taken to dryness on a rotary evaporator. The residual oil was dissolved in 100 ml. of ethyl acetate and the resulting solution was diluted to 250 ml. with petroleum ether. There was obtained 5 g. of product. Recrystallization from heptane gave 3.8 g. of pure product, mp. 114°–116°C.

Elemental Analysis for $C_{16}H_{18}N_3O_2ClS$;
Calc'd: C, 54.62; H, 5.15; N, 11.94.
Found: C, 54.84; H, 5.29; N, 12.11.

The above described compound exhibited central nervous system depressant activity evidenced by decreased motor activity, sedation, ataxia and decreased respiration at 400 milligrams per kilogram host body weight. Furthermore, the above described compound exhibited hypolipemic activity equivalent to 165 percent at 10 milligrams per kilogram host body weight and 115 percent at 50 milligrams per kilogram host body weight when compared to Atromid S.

EXAMPLE 2

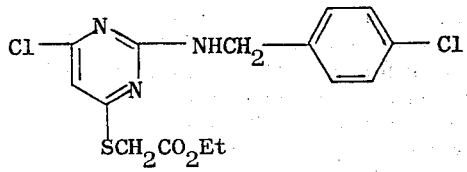

(6-Chloro-2-(p-chlorobenzylamino)-4-pyrimidinylthio)acetic ethyl ester.

A stirred mixture of 3.25 g. of 4,6-dichloro-2-(p-chlorobenzylamino)pyrimidine, 1.35 g. of ethyl mercaptoacetate and 0.95 g. of sodium bicarbonate in 50 ml. of ethanol was heated under reflux overnight. The reaction mixture was filtered. A crystalline material was deposited which amounted to 2.7 g., m.p. 122°–125°C. The analytical sample was obtained by recrystallization from ethanol, m.p. 122°–125°C.

Elemental Analysis for $C_{15}H_{15}N_3Cl_2O_2S$:
Calcd: C, 48.39; H, 4.06; N, 11.29; Cl, 19.05.
Found: C, 48.05; H, 3.95; N, 11.21; Cl, 19.06.

The above described compound exhibited central nervous system depressant activity evidenced by decreased motor activity, sedation, ataxia and decreased respiration at a dosage level as low as 40 milligrams per kilogram host body weight. The hypolipemic activity of the compound equaled 150 percent of Atromid S at 10 milligrams per kilogram and 80 percent of Atromid S at 50 milligrams per kilogram host body weight.

EXAMPLE 3

[6-(p-Chlorobenzylamino)-4-pyrimidinylthio]acetic acid ethyl ester.

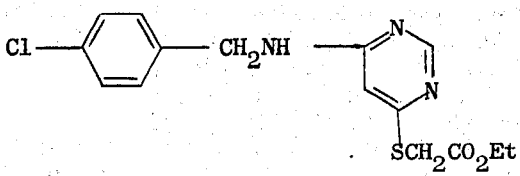

A mixture of 5.92 g. of 4,6-dichloropyrimidine, 4.8 g. of ethyl mercaptoacetate and 4.24 g. of sodium carbonate 100 ml. of ethanol was heated under reflux for 6 hours. The mixture was filtered and the filtrate was evaporated on a rotary evaporator in vacuo.

A mixture of the residual oil [(6-chloro-4-pyrimidinylthio)acetic acid ethyl ester], 5.6 g. of p-chlorobenzylamine and 4.26 g. of sodium carbonate in 150 ml. of ethanol was heated under reflux for 5 hours. The mixture was filtered and was cooled. The precipitate thus formed was collected and recrystallized from ethanol to afford 5.2 g. of product, m.p. 116°–120°C.

Elemental Analysis for $C_{15}H_{16}N_3O_2ClS$;
Calcd: C, 53.33; H, 4.77; N, 12.44.
Found: C, 53.08; H, 4.63; N, 12.40.

The above described compound exhibited central nervous system depressant activity evidenced by decreased motor activity, and decreased respiration at 12.7 milligrams per kilogram and 40 milligrams per kilogram respectively. As a hypolipemic agent, the compound of Example 3 equaled 55 percent of the activity of Atromid S at 15 milligrams per kilogram host body weight.

EXAMPLE 4

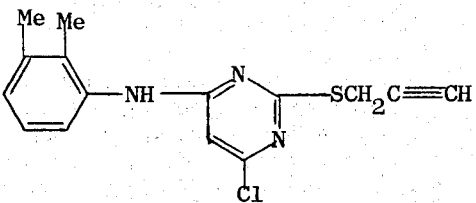

4-Chloro-2-(2-propynylthio)-6-(2,3-xylidino)pyrimidine.

To a solution of 1.68 g. (0.02 mole) of sodium bicarbonate in 50 ml. of water was added with stirring 2.88 g. (0.02 mole) of 2-thiobarbituric acid. Propargyl bromide (2.38 g., 0.02 mole) was then added and 35 ml. of ethanol to make a clear solution. The solution was stirred at room temperature for 30 minutes and was then heated to almost boiling temperature for 30 minutes and was then heated to almost boiling temperature for 1.5 hours. On cooling the precipitate was collected and recrystallized from 50 percent aqueous ethanol to afford 2.7 g. of 2-(2-propynylthio)-4,6-pyrimidinediol, m.p. 201°C. (decomp.).

Elemental Analysis for $C_7H_6N_2O_2S$:
Calc'd: C, 46.15; H, 3.32; N, 15.38.
Found: C, 46.18; H, 3.41; N, 15.03.

To a mixture of 2.7 g. of 2-(2-propynylthio)-4,6-pyrimidinediol (prepared in the preceding paragraph) in 50 ml. of phosphorus oxychloride was slowly added 2.2 g. of N,N-diethylaniline. The reaction mixture was then heated under reflux for 4 hours. The phosphorus oxychloride was removed in a rotary evaporator and the residue was poured onto 250 ml. of cracked ice. The precipitate was collected and a portion of this material was recrystallized from 50 percent aqueous ethanol to afford the analytical sample of 4,6-dichloro-2-(2-propynylthio)pyrimidine, m.p. 67°–70°C.

Elemental Analysis for $C_7H_4N_2SCl_2$:
Calc'd: C, 38.37; H, 1.84; N, 12.79.
Found: C, 38.51; H, 1.78; N, 12.65.

A stirred mixture of 8.76 g. of 4,6-dichloro-2-(2-propynylthio)pyrimidine (prepared in the preceding paragraph), 4.84 g. of 2,3-dimethylaniline and 4.24. g. of sodium carbonate in 70 ml. of ethanol was heated under reflux for 24 hours. The reaction mixture was filtered and a little water was added to the filtrate to initiate precipitation. The precipitate was collected, dried and recrystallized from benzene (petroleum ether was added to precipitate material) to give 2.1 g. of propynylthio)pyrimidine, 4.2 g. of p-chlorobenzylamine and 3.18 g. of sodium carbonate in 50 ml. of ethanol was heated under reflux for 5 hours. The reaction mixture was filtered and the filtrate was diluted with 100 ml. of water. The precipitate thus formed was collected and recrystallized from benzene (petroleum ether was added to initiate precipitation) to afford 3.3 g. of product, m.p. 85°–88°C.

Elemental Analysis for $C_{14}H_{11}N_3Cl_2S$:
Calc'd: C, 51.86; H, 3.42; N, 12.96.
Found: C, 51.57; H, 3.51; N, 12.71.

Central nervous system depressant activity was evidenced by decreased motor activity, decreased respiration and exothalmos at 40 milligrams per kilogram host body weight with evidence of diarrhea at 127 milligrams per kilogram host body weight.

EXAMPLE 6

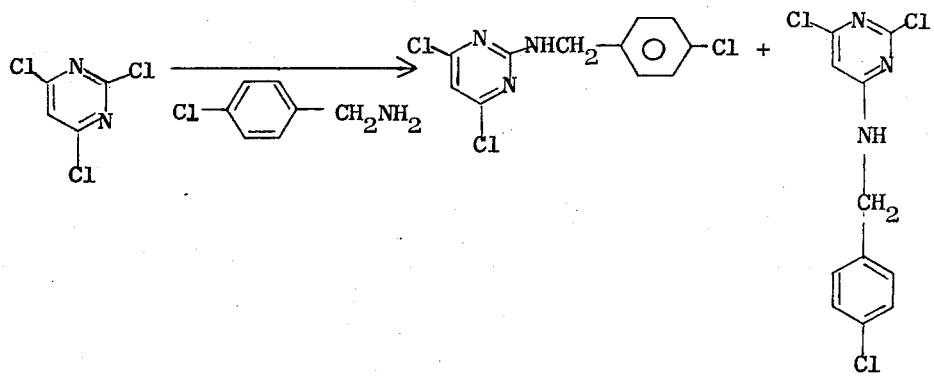

4-chloro-2-(2-propynylthio)-6-(2,3-xylidino)pyrimidine, m.p. 90°–94°C.

Elemental Analysis for $C_{15}H_{14}ClN_3S$:
Calc'd: C, 59.30; H, 4.64; N, 13.83.
Found: C, 59.07; H, 4.66; N, 13.97.

Central nervous system depressant activity was evidenced by decreased motor activity and decreased respiration at 40 milligrams per kilogram host body weight and a loss of righting reflex at 400 milligrams per kilogram host body weight. The hypolipemic activity was 125 percent of Atromid S at 40 milligrams per kilogram host body weight.

The products of the following examples, although structurally very similar to those of the preceding examples, did not exhibit hypolipemic activity at the tested dosage levels. Thus, although central nervous system depressant activity is an activity common to all the disclosed compounds, hypolipemic activity cannot be generally predicted solely from structural considerations.

EXAMPLE 5

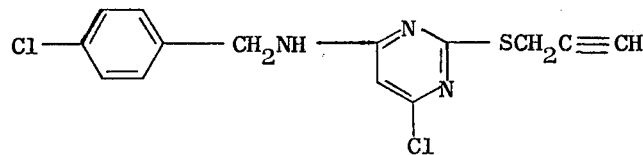

4-Chloro-6-(p-chlorobenzylamino)-2-(2-propynylthio)pyrimidine.

A stirred mixture of 6.57 g. of 4,6-dichloro-2-(2-

4,6-Dichloro-2-(p-chlorobenzylamino)pyrimidine.

A mixture of 18.3 g. of 2,4,6-trichloropyrimidine, 14.29 g. of 4-chlorobenzylamine and 10.6 g. of sodium bicarbonate in 50 ml. of ethanol was stirred at room temperature for 3 hours and was then filtered. The filter cake was washed separately with water to remove sodium bicarbonate. There was obtained 15.3 g. of 4,6-dichloro-2-(p-chlorobenzylamino)pyrimidine. An analytical sample was obtained by recrystallization from ethanol, m.p. 154°–157°C.

Elemental Analysis for $C_{11}H_8N_3Cl_3$:
Calc'd: C, 45.78; H, 2.79; N, 14.56.
Found: C, 45.81; H, 2.93; N, 14.89.

Central nervous system depressant activity was noted by decreased motor activity, sedation, ataxia and decreased respiration at 12.7 milligrams per kilogram host body weight.

EXAMPLE 7

2,6-Dichloro-4-(p-chlorobenzylamino)pyrimidine.

Water was added to the ethanol filtrate of Example 6 to the point where precipitation began. The mixture was cooled in ice and 15 g. of 2,6-dichloro-4-(p- chlorobenzylamino) pyrimidine was collected on a filter. Recrystallization of the product from aqueous ethanol gave the product with m.p. 120°–122°C.

Elemental Analysis for $C_{11}H_8N_3Cl_3$:
Calc'd: C, 45.78; H, 2.79; N, 14.56.
Found: C, 45.73; H, 2.91; N, 14.49.

Central nervous system depressant activity was observed by decreased motor activity and decrease respiration at a dosage level of 12.7 milligrams per kilogram with evidence of ataxia, ptosis and mydriasis at dosage levels at or above 127 milligrams per kilogram host body weight.

EXAMPLE 8

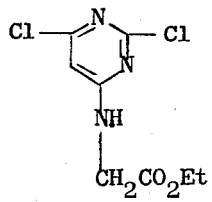

N-(2,6-Dichloro-4-pyrimidinyl)glycine ethyl ester.

To a stirred mixture of 27.8 g. (0.2 mole) of glycine ethyl ester hydrochloride and 42.4 g. (0.4 mole) of sodium carbonate in 300 ml. of ethanol was added 36.6 g. (0.2 mole) of 2,4,6-trichloropyrimidine. After stirring at room temperature for 2 hours the mixture was filtered. The filtrate was diluted with 300 ml. of water and the precipitate thus formed was collected, dried, and triturated with 600 ml. of boiling petroleum ether. The insoluble material was filtered off and recrystallized from ethanol-petroleum ether to afford 4.7 g. of product, m.p. 89°–91°C.

Elemental Analysis for $C_8H_9N_3Cl_2O_2$:
Calc'd: C, 38.42; H, 3.63; N, 16.80.
Found: C, 38.48; H, 3.67; N, 16.71.

Central nervous system depressant activity was noted by decreased motor activity and decreased respiration at 12.7 milligrams per kilogram host body weight.

EXAMPLE 9

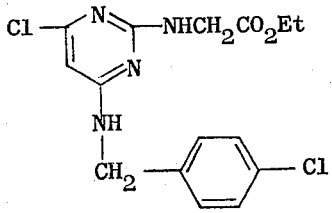

N-[4-Chloro-6-(p-chlorobenzylamino)-2-pyrimidinyl]glycine ethyl ester.

The petroleum ether filtrate from the Example 8 was cooled in ice to deposit a solid which was recrystallized from pentane to give 2.9 g. of N-(4,6-dichloro-2-pyrimidinyl)glycine ethyl ester, m.p. 70°–72°C.

Elemental Analysis for $C_8H_9N_3Cl_2O_2$:
Calc'd: C, 38.42; H, 3.63; N, 16.80.
Found: C, 38.19; H, 3.66; N, 16.45.

A stirred mixture of 6.1 g. (0.024 mole) of N-(4,6-dichloro-2-pyrimidinyl)glycine ethyl ester, 3.4 g. (0.024 mole) of p-chlorobenzylamine and 2.6 g. (0.024 mole) of sodium carbonate in 100 ml. of ethanol was heated under reflux for 5 hours. The reaction mixture was filtered and the filtrate on cooling gave a precipitate. The precipitate was collected and recrystallized twice from benzene to give 4.6 g. of product, m.p. 132°–135°C.

Elemental Analysis for $C_{15}H_{16}N_4O_2Cl_2$:
Calc'd: C, 50.72; H, 4.54; N, 15.77.
Found: C, 50.54; H, 4.63; N, 15.82.

Central nervous system depressant activity was noted in decreased motor activity and decreased respiration at a dosage level of 12.7 milligrams per kilogram host body weight with evidence of cyanosis and ptosis at a dosage level at or above 127 milligrams per kilogram host body weight.

EXAMPLE 10

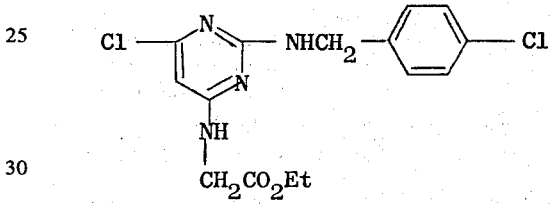

METHOD A

N-[6-Chloro-2-(p-chlorobenzylamino)-4-pyrimidinyl]glycine ethyl ester.

A stirred mixture of 10.0 g. (0.04 mole) of N-(2,6-dichloro-4-pyrimidinyl)glycine ethyl ester, prepared in Example 8, 5.6 g. (0.04 mole) of p-chlorobenzylamine and 4.24 g. (0.04 mole) of sodium carbonate in 100 ml. of ethanol was heated under reflux for 6 hours. The reaction mixture was filtered and the filtrate was cooled in ice. The precipitate thus formed was collected and recrystallized from benzene with petroleum ether being added to initiate precipitation to give 4.1 g. of product, m.p. 168°–170°C.

Elemental Analysis for $C_{15}H_{16}N_4O_2Cl_2$:
Calc'd: C, 50.72; H, 4.54; N, 15.77.
Found: C, 50.73; H, 4.42; N, 15.53.

METHOD B

A stirred mixture of 2.9 g. of 4,6-dichloro-2-(p-chlorobenzylaminio)pyrimidine, prepared in Example 6, 1.4 g. of ethyl glycinate hydrochloride and 1.0 g. of sodium carbonate was heated under reflux overnight. The reaction mixture was filtered and the filtrate cooled in ice. Addition of water to the filtrate caused a precipitate to form. Two recrystallizations of this material from heptane gave a product with m.p. 163°–166°C. The infrared spectrum of this material was identical with that prepared by Method A.

Central nervous system depressant activity was noted in decreased motor activity and decreased respiration at 12.7 milligrams per kilogram host body weight with evidence of cyanosis and ptosis at a dosage level at or above 127 milligrams per kilogram host body weight.

EXAMPLE 11

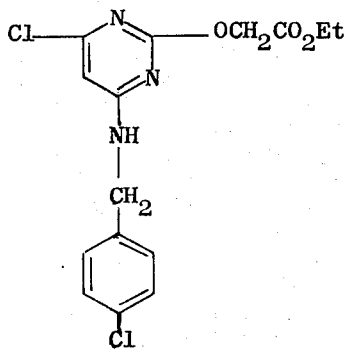

[4-Chloro-6-(p-chlorobenzylamino)-2-pyrimidinyloxy]acetic acid ethyl ester.

To 4.2 g. of ethyl glycolate in 50 ml. of anhydrous tetrahydrofuran was added 1.7 g. of sodium hydride oil dispersion (57 percent) with stirring. There was added after 20 minutes 11.5 g. of 2,4-dichloro-6-(p-chlorobenzylamino)pyrimidine.

The reaction mixture was heated under reflux for 3 hours and filtered. The filtrate was taken to dryness on a rotary evaporator. On scratching the residual oil a crystalline product was obtained. Recrystallization from ethanol afforded 1.7 g. of product, m.p. 114°–116°C.

Elemental Analysis for $C_{15}H_{15}Cl_2N_3O_3$:
Calc'd: C, 50.58; H, 4.24; N, 11.80; Cl, 19.91.
Found: C, 50.76; H, 4.17; N, 11.92; Cl, 19.85.

Central nervous system depressant activity was noted by decreased motor activity and decreased respiration at 12.7 milligrams per kilogram host body weight with evidence of sedation and ataxia at dosages at or above 127 milligrams per kilogram host body weight.

EXAMPLE 12

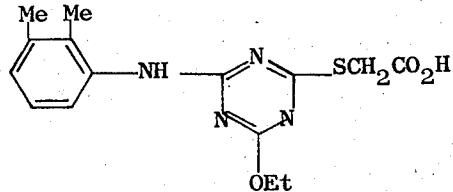

4-Ethoxy-6-(2,3-xylidino)-s-triazin-2-ylthio)acetic acid

To a stirred solution of 9.0 g. (0.05 mole) of cyanuric acid chloride in 250 ml. of benzene was added dropwise over 30 minutes at room temperature 12.0 g. (0.1 mole) of 2,3-dimethylaniline. The precipitate thus formed was filtered off and the filtrate was diluted with petroleum ether. The solid that was formed was collected and recrystallized from benzene (petroleum ether was added to initiate precipitation) to give 2.8 g. of 2,4-dichloro-6-(2,3-xylidino)-s-triazine, m.p. 186°–191°C.

Elemental Analysis for $C_{11}H_{10}N_4Cl_2$:
Calc'd: C, 49.09; H, 3.74; N, 20.82.
Found: C, 48.33; H, 3.76; N, 20.73.

A stirred mixture of 4.0 g. of 2,4-dichloro-6-(2,3-xylidino)-s-triazine, 1.59 g. of sodium carbonate and 1.80 g. of ethyl mercaptoacetate in 75 ml. of ethanol was heated under reflux for 6 hours. The reaction mixture was then filtered and the filtrate was evaporated on the rotary evaporator. The residue was dissolved in benzene and the benzene solution was diluted with petroleum ether. The precipitate thus formed was collected and heated for a few minutes with 20 ml. of 30 percent sodium hydroxide and enough ethanol to make a solution. The mixture was acidified with concentrated hydrochloric acid and the precipitate was collected and recrystallized twice from ethanol to give 0.75 g. of product, m.p. 217°–220°C. (decomp.). Elemental Analysis for $C_{15}H_{18}N_4O_3S$:
Calcd: C, 53.88; H, 5.42; N, 16.75.
Found: C, 53.76; H, 5.30; N, 16.74.

Central nervous system depressant activity was noted by decreased motor activity and decreased respiration at 40 milligrams per kilogram host body weight with sedation, ataxia and ptosis appearing at dosage levels at or above 127 milligrams per kilogram host body weight.

EXAMPLE 13

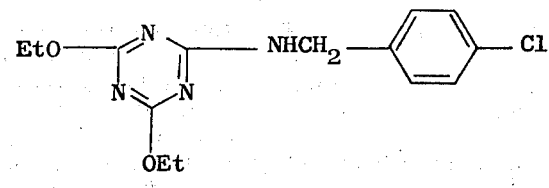

2-(p-Chlorobenzylamino)-4,6-diethoxy-5-triazine.

To a stirred mixture of 1.41 g. of p-chlorobenzylamine and 1.06 g. of sodium carbonate in 40 ml. of ethanol at 0°–5°C. was added 1.84 g. of cyanuric chloride. The mixture was stirred at this temperature for 1 hour. The reaction mixture was then filtered and the filtrate was diluted with water. The precipitate thus formed was collected and recrystallized from aqueous ethanol to give 0.4 g. of product, m.p. 132°–135°C.

Elemental Analysis for $C_{14}H_{17}N_4Cl_2O_2$:
Calc'd: C, 54.46; H, 5.55; N, 18.14.
Found: C, 54.54, H, 5.64; N, 17.81.

Central nervous system depressant activity was noted by decreased motor activity at 400 milligrams per kilogram host body weight.

EXAMPLE 14

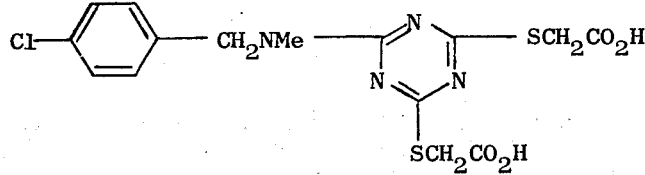

(6-[(p-Chlorobenzyl)methylamino]-s-triazine-2,4-diyldithio) diacetic acid.

To a stirred solution of 5.52 g. (0.03 mole) of cyanuric acid chloride in 150 ml. of benzene was added dropwise over 30 minutes at room temperature 9.3 g. (0.06 mole) of N-methyl-p-chlorobenzylamine. The reaction mixture was filtered and the filtrate was reduced on the rotary evaporator to give 2,4-dichloro-6-(p-chlorobenzyl)methylamino)-s-triazine as an oil which was used without purification in the next step.

A stirred mixture of 9.12 g. of 2,4-dichloro-6-(p-chlorobenzyl)methylamino)-s-triazine, 7.21 g. of ethyl mercaptoacetate and 6.36 g. of sodium carbonate in 100 ml. of ethanol was heated under reflux for 6 hours. The reaction mixture was then filtered and the filtrate was taken down on a rotary evaporator. The residue was heated for a few minutes with 50 ml. of 30 percent sodium hydroxide and enough ethanol to make a solution. The mixture was acidified with concentrated hydrochloric acid and the precipitate was collected and recrystallized from ethanol-petroleum ether to afford 1.5 g. of product, m.p. 178°–180°C. (decomp.).

Elemental Analysis for $C_{15}H_{15}N_4O_4S_2Cl$:
Calc'd: C, 43.42; H, 3.64; N, 13.50.
Found: C, 43.36; H, 3.77; N, 13.16.

Central nervous system activity was noted by decreased motor activity and decreased respiration at 127 milligrams per kilogram host body weight.

EXAMPLE 15

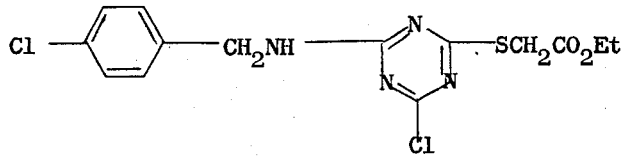

[4-Chloro-6-(p-chlorobenzylamino)-s-triazin-2-ylthio]acetic acid ethyl ester.

To a stirred solution of 18.4 g. (0.1 mole) of cyanuric acid chloride in 500 ml. of benzene was added dropwise over 1 hour at room temperature 28 g. (0.2 mole) of p-chlorobenzylamine. After addition of the amine, the thick precipitate was filtered off. The filtrate was diluted to twice its volume with petroleum ether and the precipitate thus formed was filtered off. A further dilution of this filtrate with petroleum ether gave a solid which was collected and recrystallized from benzene (petroleum ether was added to induce precipitation) to give 3.4 g. of 2,4-dichloro-6-(p-chlorobenzylamino)-s-triazine, m.p. 151°–156°C.

Elemental Analysis for $C_{10}H_7N_4Cl_3$:
Calc'd: C, 41.48; H, 2.44; N, 19.35.
Found: C, 41.66; H, 2.79; N, 19.00.

A stirred mixture of 9.2 g. of 2,4-dichloro-6-(p-chlorobenzylamino)-s=triazine prepared, in the preceding paragraph, 3.86 g. of ethyl mercaptoacetate and 3.32 g. of sodium carbonate in 200 ml. of ethanol was heated under reflux for 6 hours. The reaction mixture was filtered and the filtrate was cooled in ice. The solid thus formed was collected and recrystallized from ethanol to afford 2.5 g. of product, m.p. 143°–147°C.

Elemental Analysis for $C_{14}H_{14}N_4Cl_2SO_2$:
Calc'd: C, 45.05; H, 3.78; N, 15.01.
Found: C, 45.30; H, 4.09; N, 14.81.

We claim:

1. A compound of the formula:

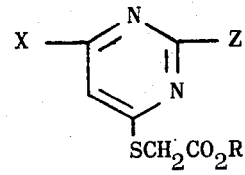

in which

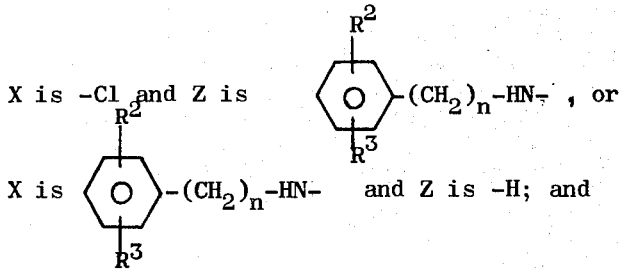

R is -H or lower alkyl; wherein
$R^2$ is -H or lower alkyl;
$R^3$ is lower alkyl or —Cl; and
$n$ represents one of the integers 0 and 1.

2. The compound of claim 1 which is [6-chloro-2-(2,3-xylidino)-4-pyrimidinylthio]acetic acid ethyl ester.

3. The compound of claim 1 which is [6-chloro-2-(p-chlorobenzylamino)-4-pyrimidinylthio]acetic acid ethyl ester.

4. The compound of claim 1 which is [6-(p-chlorobenzylamino)-4-pyrimidinylthio]acetic acid ethyl ester.

* * * * *